(12) United States Patent
Leumann et al.

(10) Patent No.: US 8,242,325 B2
(45) Date of Patent: Aug. 14, 2012

(54) WOUND COVERING AND ITS METHOD OF PRODUCTION BY EXTRUSION COATING

(75) Inventors: Manuel Leumann, Beinwil am See (CH); Andreas Dobmann, Oberkirch (CH)

(73) Assignee: Collano AG, Sempach-Station (CH)

( * ) Notice: Subject to any disclaimer, the term of this patent is extended or adjusted under 35 U.S.C. 154(b) by 405 days.

(21) Appl. No.: 12/161,713

(22) PCT Filed: Oct. 27, 2006

(86) PCT No.: PCT/EP2006/010382
§ 371 (c)(1),
(2), (4) Date: Jul. 22, 2008

(87) PCT Pub. No.: WO2007/090444
PCT Pub. Date: Aug. 16, 2007

(65) Prior Publication Data
US 2010/0222730 A1  Sep. 2, 2010

(30) Foreign Application Priority Data
Feb. 6, 2006 (EP) .................................... 06101315

(51) Int. Cl.
*A61F 13/00* (2006.01)
*B29D 7/00* (2006.01)
*B32B 33/00* (2006.01)

(52) U.S. Cl. .................... 602/46; 264/45.9; 264/171.11

(58) Field of Classification Search ................. 264/45.9, 264/46.4, 173.12, 173.11, 173.16, 45.8, 171.13, 264/46.1, 37.32; 602/41–46, 56; D24/189; 128/848, 888, 889, 849
See application file for complete search history.

(56) References Cited

U.S. PATENT DOCUMENTS

| | | | | |
|---|---|---|---|---|
| 3,551,243 A | * | 12/1970 | Schuur Gerrit et al. | . 156/244.14 |
| 3,668,050 A | * | 6/1972 | Donnelly | ...................... 128/849 |
| 4,854,995 A | | 8/1989 | Kasper et al. | |
| 5,147,338 A | | 9/1992 | Lang et al. | |
| 5,203,764 A | | 4/1993 | Libbey et al. | |
| 5,753,342 A | | 5/1998 | McBride et al. | |

(Continued)

FOREIGN PATENT DOCUMENTS

DE   3515580   11/1985

(Continued)

OTHER PUBLICATIONS

Stokes, "Joining Methods for Plastics and Plastic Composites", Polymer Engineering and Science, vol. 29, No. 19, Oct. 1989, pp. 1310-1324, XP002418754.

*Primary Examiner* — Patricia Bianco
*Assistant Examiner* — Ophelia Hawthorne
(74) *Attorney, Agent, or Firm* — Shoemaker and Mattare

(57) ABSTRACT

The invention relates to a production method for a foam wound dressing with an outer germ barrier, in particular a film layer, and to a wound dressing obtained by such a method. In the method according to the invention, the germ barrier is generated by means of extrusion directly on the foam support. This results in a more reliable union between foam layer and germ barrier, without thereby compromising the absorbency of the foam in respect of wound exudate. The proposed method is simple and inexpensive and is able to satisfy all the requirements of the medical sector (e.g. freedom from solvents).

13 Claims, 2 Drawing Sheets

U.S. PATENT DOCUMENTS

| | | | |
|---|---|---|---|
| 6,165,625 A | 12/2000 | Sommers et al. | |
| 6,245,271 B1 * | 6/2001 | Jacobs et al. | 264/154 |

FOREIGN PATENT DOCUMENTS

| | | |
|---|---|---|
| EP | 0059048 | 9/1982 |
| EP | 0059049 | 9/1982 |
| EP | 0545565 | 6/1993 |
| EP | 0651984 | 5/1995 |
| JP | 06-022999 | 2/1994 |
| JP | 2002-67206 | 3/2002 |
| JP | 2003-53894 | 2/2003 |
| WO | 91/01706 | 2/1991 |
| WO | 95/15135 | 6/1995 |

* cited by examiner

WOUND COVERING AND ITS METHOD OF PRODUCTION BY EXTRUSION COATING

The invention pertains to the field of wound covers based on foam materials, especially methods of production for such wound covers.

Wound covers are intended to fulfill a multiplicity of functions: Thus, for example, the assurance of germ imperviosity and the establishment of a physiological healing environment, preference here being nowadays given, in the case of secondarily healing wounds, to a moist healing environment. Further, the wound cover ought not to exhibit cytotoxicity or allergenicity and ought to be able to be changed/removed without trauma. Further, excess wound exudate must be conducted away from the wound.

In present-day wound management the use of foam-based wound covers is on the increase, particularly for chronic wounds. Foam-based wound covers of this kind have the advantage that wound exudate can be reliably removed from the wound by virtue of the foam's absorbency. As set against old-established wound covers such as gauze and muslin bandages, for example, and so on, foam-based wound covers thus afford the advantage of a greater capacity to absorb wound exudate, plus the further advantage that there is no sticking to the wound and therefore that dressings can be changed painlessly.

On the facing remote from the wound these foam-based wound covers are generally lined with a germ barrier, typically a film. This germ barrier on the one hand constitutes a protection against inwardly penetrating bacteria, and also, moreover, regulates gas exchange with the ambient environment. By tailoring the water vapor permeability of this germ barrier it is possible to ensure the prevalence of a sufficiently moist environment beneath the wound cover, without maceration of the skin. This germ barrier, moreover, protects clothing and other dressing material from emergent wound exudate.

At the present time, germ barriers of this kind, films for example, are bonded to the foam underply by applying either solvent-based adhesives (typically by spraying) or hot-melt adhesives. The adhesive may in this case be applied either to one side (typically to the film) or to both sides, in other words to the film and to the foam. An alternative possibility, for example, is to insert a heat-activable adhesive web between film and foam, thereby producing the bond. When employing an adhesive, however, it is always necessary to produce an interlayer in order to ensure the bond between foam and film.

It is always critical in this respect that the adhesive layer must not hinder the transport of water vapor; in general the permeability should be more than 1000 $g/m^2/day$. Such permeability can be achieved, for example, via an open coating pattern with adhesive or by a film of adhesive that is applied over the full area but is permeable for water vapor.

Ensuring sufficient water vapor permeability through the adhesive layer in practice during production represents a problem which should not be underestimated, whereas permeability through the film and the foam can be determined and adjusted with simple routine experiments. Moreover, the necessary adhesive layer has the effect of making production more expensive overall. Furthermore, the bonding of film and foam by a layer of adhesive is often not convincing in practice, since again and again there are instances of detachment of the film from the foam.

From U.S. Pat. No. 5,147,338 it is known, in the case of a wound cover, to apply a polyurethane film to a polyurethane foam by spraying. By this means it is possible to do away with the abovementioned layer of adhesive. The spraying of a polyurethane film onto the foam, however, has a multiplicity of disadvantages: First, uniform application is difficult to ensure. Second, the sprayed-on polyurethane material exhibits significant penetration into the foam, which can considerably lower the foam's capacity to absorb wound exudate. Furthermore, in order to ensure the sprayability of polyurethane materials, solvent must be added; solvent residues in the wound cover, however, cannot be tolerated.

U.S. Pat. No. 3,668,050 discloses a surgical drape having an operation aperture. The surgical drape may feature a film layer extruded onto a foam material. The foam material is disposed on the side remote from the wound and is intended, among other things, to prevent surgical instruments which have been placed thereon from slipping.

EP 651 984 discloses a patch/plaster featuring an outer, nonporous film layer and a layer of pressure-sensitive adhesive which faces the body and into which a porous layer of, for example, foam with a thickness in the range from 0.01 to 0.5 mm has been imbedded. The pressure-sensitive adhesive in this case penetrates down to the outer film layer; the imbedment of the porous layer makes the attachment of the pressure-sensitive adhesive to the patch/plaster stronger.

It is an object of the present invention, therefore, to avoid the disadvantages of the known art, more particularly to provide a foam-based wound cover and a production method for a foam-based wound cover that is simple and inexpensive to implement, contains or leaves no residues (e.g., solvent residues) in the finished product, and results in ensuring a bond between foam and film that is outstanding and has long-term robustness, without the absorption capacity of the foam for wound exudate being lowered.

This object is achieved by means of a wound cover and a method of producing such a wound cover, as defined in the claims.

The method of the invention of producing an at least two-layer, more particularly substantially uninterruptedly two-dimensional article, more particularly a wound cover, comprising a first layer of a foam material, having a first main area and more particularly a second main area; and a second layer as germ barrier, more particularly of a film material, which second layer is directly adjacent to the first main area of the first layer, comprising the following steps:

providing the foam material of the first layer, more particularly in a thickness between 1 mm to 10 mm, preferably between 3 mm to 5 mm;

applying, more particularly extruding, at least one thermoplastic material onto a main area of the foam material at a temperature above the softening temperature of the thermoplastic material (2), material which then solidifies to form the second layer.

Preferably the first layer of a foam material in this arrangement is not imbedded into a pressure-sensitive adhesive layer, in other words in contrast to aforementioned document EP 651 984.

Alternatively and/or additionally it is likewise possible in the context of the invention to heat the first layer of a thermoplastic foam material to a temperature above the softening temperature. In that case thermoplasticity of the material for the second layer is not mandatory. A disadvantageous aspect of methods involving heating of the foam material, however, is that the combining with the second layer then takes place under pressure, which, in the case of inadequately set boundary conditions for the operation, might adversely affect the structure of the heated foam material and hence, where appropriate, the capacity to absorb wound exudate and the water vapor permeability.

By the two "main areas" of the foam material of the first layer are meant here those areas which, in the case of as-intended use as a wound cover, run substantially parallel to the covered skin surface of the wounded patient, on the wound-facing side and on the side remote from the wound.

Areas of the multilayer material of the invention that are understood to be "substantially uninterrupted" are those which have no openings that would run significantly counter to establishing the desired moist environment beneath the wound cover in as-intended use. The criterion "substantially uninterrupted" therefore does not rule out the presence, for example, of suitably dimensioned perforation lines allowing individual pieces to be separated off by tearing.

Surprisingly it has emerged that, more particularly by the extrusion of the germ barrier, preferably of a film material, directly (in other words without an interlayer of adhesive) onto the foam material, it is possible to produce wound covers which exhibit not only outstanding bond strength but also only minimal penetration of the germ-barrier or film material into the foam. The absorption capacity of the foam is therefore not adversely affected in the way observed, in contrast, in the case of film material applied by spraying. The material for producing the germ barrier need not be present in solution for extrusion (in contrast to the spraying technique), as a result of which there are no residues of solvents in the finished product. Production, moreover, is simple to operate; the layer thickness of the applied material can be reliably set and kept constant with conventional extrusion lines (more particularly with common slot dies). With appropriately chosen operating conditions it is possible, alternatively or additionally, to employ methods other than extrusion, such as flame lamination, calendaring, ultrasonic welding, for example, and so on. Suitable methods are familiar per se to the skilled worker. In the context of the present invention it should in any case be ensured that the operating conditions are chosen such that the above-described requirements concerning the absorption capacity of the foam material of the first layer for the wound exudate, the water vapor permeability of both layer, and the quality of the second layer as a germ barrier are not impaired.

In further preferred embodiments of the invention a polyurethane foam is provided as the foam material. The foam material provided is preferably hydrophilic. With particular preference the foam material is substantially open-celled. It is possible with preference to choose an average pore size in the range from 0.02 mm to 0.2 mm. Suitable and particularly preferred hydrophilic, polyurethane-based foam materials are known to the skilled worker and available on the market (examples being Vivo MCF 03 from Corpura B.V., 4879 NE Etten-Leur, The Netherlands; or 3014 from Polymer Health Technology, Ebbw Vale, NP23 8XE, United Kingdom).

In a further advantageous embodiment of the invention the foam material is provided in a thickness between 1 mm to 10 mm, preferably between 3 mm and 5 mm. Such thicknesses have proven to be an outstanding tradeoff between requisite absorption capacity for wound exudate and handleability of the wound cover.

In particularly advantageous embodiments of the invention the at least one material is extruded in step b) onto the foam material in such a way as to form a second layer having a thickness between 15 μm to 100 μm, preferably between 20 μm to 40 μm. Thicknesses within the stated ranges have little or no effect on the handleability of the wound cover, and within this thickness range the aforementioned controlling of the water vapor permeability of the resulting film can be adapted to all of the requirements that occur in practice.

It has been found particularly advantageous that the extrusion of the at least one material in step b) takes place at a temperature in the range between 150° C. and 240° C., preferably between 180° C. and 220° C., more particularly between 200° C. and 210° C.

In a further, particularly preferred embodiment it is possible to produce in step b) two layers, more particularly by extrusion of two materials, either sequentially or by means of coextrusion. Also possible is the application of a first film layer by means of extrusion and of a further layer by means, for example, of spraying. The invention makes it possible more particularly to produce, for example, a thin, foam-facing layer which is optimized for adhesion to the foam; layer thicknesses of 5 μm to 10 μm have proven to be sufficient already for this purpose. Subsequently, as an outer, second layer, it is possible to apply a layer having, for example, relatively high mechanical strength (typically in a thickness of about 10 μm to 20 μm), or to coextrude it simultaneously. In this way it is therefore possible, for example, to produce film layers which are composed of at least two component layers, in which case the film layer overall can be very thin, while nevertheless exhibiting very good adhesion to the foam material and also a softness to the touch. Moreover, through the use of two different layers, it is also possible to control the water vapor permeability via the selection of the material for the additional layer, independently of the overall thickness of the film layer.

In a further embodiment of the invention the at least one material can be foamed during and/or after application, more particularly extrusion in step b). The foaming of a material during and/or after extrusion is familiar per se to the skilled worker and can be accomplished with conventional means (through the addition, for example, of a blowing agent such as azodicarbonamide or by subsequent action of heat). Advantageously it would be possible, for example, to extrude a first, foamed layer onto the foam, having a pore size lower than that of the underlying foam layer. Subsequently (or else simultaneously by coextrusion) it is then possible to apply the concluding layer, a film layer for example. As a result of the decrease in porosity and/or transition from open-celled to closed-celled material, which is therefore not abrupt but, rather, graduated, it is possible to achieve a further improvement in the adhesion between wound-facing foam and outer film, while also resulting in a visually smoother side remote from the wound, as is normally desired.

On the first, wound-side layer of a foam material it is of course also possible, more particularly by coextrusion, to produce a second layer, as a germ barrier, made of a foam material, even without additional, outer (film) layer(s), for example. If, then, a foam is employed as a germ barrier, the foam in question must be a suitable, substantially closed-celled foam, in order to ensure the germ barrier effect and also, more particularly, the establishment of the desired moist environment beneath the wound cover. Generating a closed-celled foam by and/or after extrusion is familiar to the skilled worker, as set out above. Any boundary conditions to be adapted for the extrusion and/or the heat treatment can be readily determined by the skilled worker in routine experiments.

With particular preference, after the extrusion of the material in step b), the extrudate is pressed onto the first layer, or the foam, by means of a cooled roll. In this case, however, there is minimal, if any, penetration of the foam, since the extrudate is in a pre-shaped form when it impinges on the foam, and, in particular, the viscosity of the melt is already very high.

It is further preferred to provide thermoplastic polyurethane material, more particularly a polyether polyurethane, in step b). Thermoplastic polyether polyurethanes with approval for the medical sector are known to the skilled worker and available on the market. Particularly suitable thermoplastic materials have a melt flow index (MFI) in accordance with ISO 1133 of between 5 and 50 g/10 min at 170° C. with a die weight of 21.6 kg.

A further aspect of the invention relates to a two-layer two-dimensional article, more particularly a wound cover, comprising a first layer of a foam material, and a second layer as germ barrier, more particularly of a film material, which second layer is directly adjacent to a main area of the first layer, and, in the case of a pore size of the substantially open-celled foam material in the range from 0.02 mm to 0.2 mm, the material of the second layer has penetrated not more than 0.01 mm into the foam material. A minimal depth of penetration of this kind can be brought about more particularly by a method as described in detail above, whereas with conventional spray application of polyurethane solutions the resulting depth of penetration is at least about 0.05 mm.

An additional aspect of the invention relates to the use of an extrusion process in the production of a film layer directly on a foam-based wound cover.

The invention is elucidated below by means of exemplary embodiments and figures, without the subject matter of the invention being restricted to these exemplary embodiments.

Figure 1:
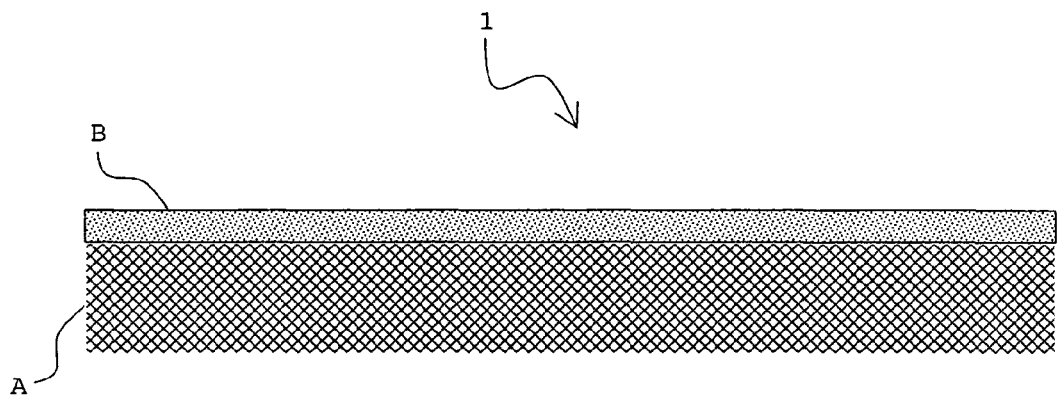
FIG. 1 shows a wound cover with foam layer and outer film.
Figure 3:
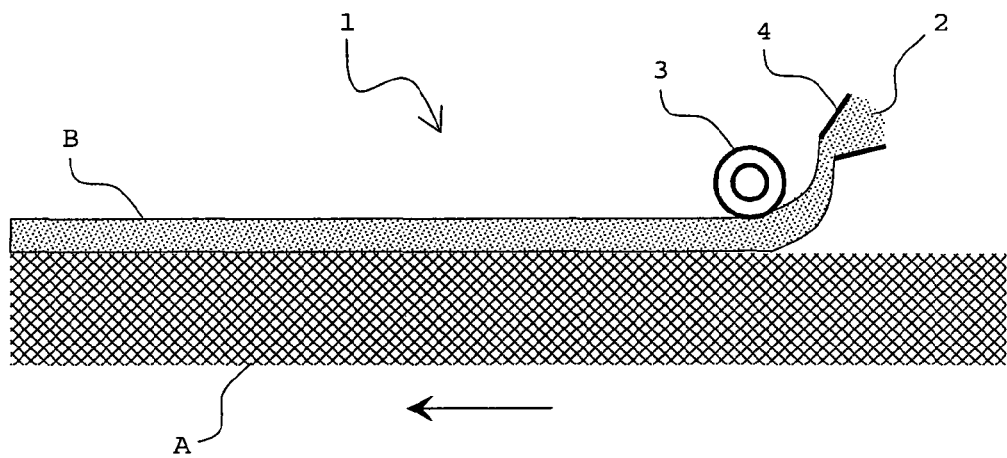
FIG. 3 shows a production method, diagrammatically.

FIG. 1 shows, diagrammatically and in simplified form, a wound cover 1 of the invention, obtainable with the method described in detail above and illustrated in FIG. 3, comprising a wound-facing first layer A of a foam material, and a second layer B, as germ barrier, of a film material. The two layers A and B are joined without an interlayer; in particular there is no layer of adhesive between the first layer A and the second layer B. Particularly reliable bonds are obtained when the materials of the first layer A and second layer B are chemically related. With advantage the first layer A is a hydrophilic polyurethane foam, and layer B is a layer of polyether polyurethane; on account of the similar chemical nature of the two layers it is possible to obtain a particularly stable bond.

Figure 2:
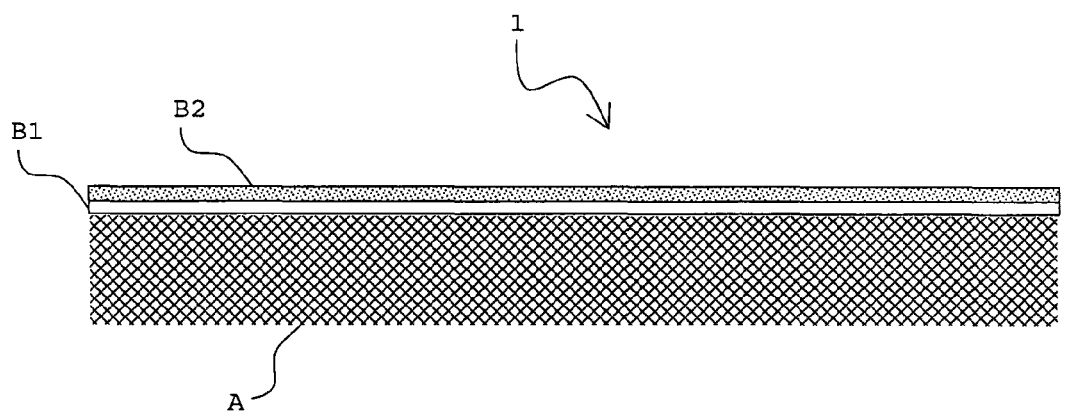
FIG. 2 shows a wound cover with foam layer and two outer film layers.

FIG. 2 shows an embodiment of a wound cover of the invention in which, on a first layer A of a foam material, a second layer has been applied which encompasses the component layers B1 and B2. The layers B1 and B2 can be produced either together, by means of coextrusion for example (or sequential extrusion). Also possible is the production of layer B1 only by means of extrusion, with the layer B2 being sprayed on subsequently, for example. The layer B2 may but need not necessarily be applied two-dimensionally; in particular it may also represent an imprint, comprising written indicia such as manufacturer details, brand names or else cutting lines to facilitate accurate trimming of the wound cover.

FIG. 3 illustrates, diagrammatically, one embodiment of the production method of the invention, with reference to a wound cover. A first layer A of a foam material is conveyed in a conventional, suitable extrusion line (not shown in detail) along the direction of the arrow. In order to ensure reliable conveying of the foam material it is possible where appropriate to provide a rigid support material for the layer A. Via a die 4, typically a slot die, a thermoplastic material (in this case a thermoplastic polyether polyurethane) is extruded, typically at a temperature between 150° C. and 240° C., preferably at 180° C. and 220° C. The nozzle 4 in this case has no direct contact with the layer A; instead, the material 2 leaves the die in pre-shaped form and is deposited, to some extent, on the layer A and then pressed onto the layer A, preferably with a cooled roll 3, in such a way that a firm bond is formed between layer A and the layer B formed from the material 2.

Figure 4:
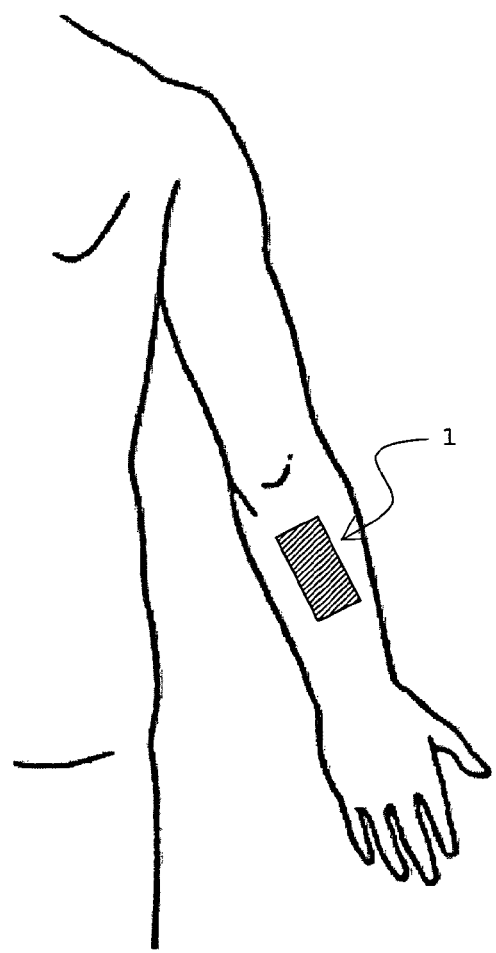
FIG. 4 shows a wound cover on an arm.

FIG. 4 shows a wound cover 1 in accordance with the invention in use, in this case, by way of example, as a cover on a wound on an arm. In this plan view the layer B remote from the wound is shown with shading. Located on the wound-facing side (in the figure), hidden, is the layer A of a foam material. The wound cover can be fixed, for example, with pressure-sensitive adhesive strips. The size of the wound cover is to be chosen in conformity with the respective wound size, either by using pre-processed wound covers or by separation (by tearing along perforations, for example), more particularly by trimming (for example, along marks printed preferably on the layer A) of a suitably sized wound cover from a larger unit.

Wound dressings obtained with the method of the invention were analyzed for the strength of the bond between film and foam and were compared with a current commercial product. The material used to produce the film layer (layer B) was Perlathane® D16N85 (manufacturer: Merquinsa), MFI 10 g/10 min at 170° C. (21.6 kg die weight), extrusion temperature 205° C.; the foam underply used in each case (layer A) is indicated in Table 1. The test methods used in this context were as follows:

Test Method 1: Adhesion 5 ml of an aqueous 0.9% NaCl solution are applied to the polyurethane foam side of 100 $cm^2$ (10×10 cm sample) of the assembly formed from layer A and layer B. The wetted samples are subsequently stored at 40° C. in a saturated water vapor atmosphere for 24 h. Following the removal of the test specimens, they are cooled to room temperature for 10 minutes. Subsequently the adhesion between polyurethane film and polyurethane foam is assessed qualitatively by hand. Assessed for the purpose of comparison are samples which have not been subjected to hot and humid storage. The adhesion found is classed according to a ratings system (1=unusable, 2=weak, 3=inadequate, 4=adequate, 5=good, 6=excellent).

Test Method 2: Imperviosity 5 ml of an aqueous 0.9% NaCl solution colored with 0.1% of methylene blue are applied to the polyurethane foam side of 100 $cm^2$ (10×10 cm sample) of the assembly formed from layer A and layer B. After hour (room temperature) the imperviosity on the polyurethane film side (layer B) is assessed visually. The imperviosity found is classed according to a ratings system (1=unusable, 2=weak, 3=inadequate, 4=adequate, 5=good, 6=excellent).

The results obtained are reported in Table 1:

TABLE 1

| Assessment of adhesion and imperviosity of inventive wound dressings. | | | |
| --- | --- | --- | --- |
| PU film extruded onto: | Vivo MCF 03 (Corpura B.V.) | Foam 3014 (Polymer Health Technology) | Reference sample 3M Foam Dressing (Art. 90601) |
| Adhesion between foam and film (blank value) | 6 | 6 | 5 |

TABLE 1-continued

Assessment of adhesion and imperviosity of inventive wound dressings.

| PU film extruded onto: | Vivo MCF 03 (Corpura B.V.) | Foam 3014 (Polymer Health Technology) | Reference sample 3M Foam Dressing (Art. 90601) |
|---|---|---|---|
| Adhesion between foam and film after 24 h humid storage at 40° C. | 5 | 5 | 3-4 |
| Imperviosity after 1 hour | 6 | 6 | 6 |

It is evident that the strength of the bond between layer A (foam) and layer B (film) in the case of the inventive wound dressings or through the production method of the invention is improved for such a wound dressing under typical service load.

The invention claimed is:

1. A method of producing a substantially uninterrupted wound cover, said wound cover comprising
   a first layer of a foam material, having a first main area and a second main area; and
   a second layer of a film material as a germ barrier, which second layer is directly adjacent to the first main area of the first layer,
   said method comprising steps of:
   i) providing the foam material of the first layer;
   ii) extruding at least one thermoplastic material onto a main area of the foam material at a temperature above the softening temperature of the thermo-plastic material, and solidifying the thermoplastic material to form the second layer, wherein the thermoplastic material of the second layer penetrates not more than 0.01 mm into the foam material of the first layer.

2. The method of claim 1, wherein the foam material of the first layer is a polyurethane foam.

3. The method of claim 1, wherein the first layer is hydrophilic.

4. The method of claim 1 wherein the foam material of the first layer is open-celled.

5. The method of claim 1, wherein the at least one thermoplastic material is extruded in step ii) onto the foam material in such a way as to form a second layer having a thickness between 15 µm to 100 µm.

6. The method of claim 1, wherein the extrusion of the at least one thermoplastic material takes place in step ii) at a temperature in the range between 150° C. and 240° C.

7. The method of claim 1, wherein two layers of thermoplastic material are produced during the extruding step.

8. The method of claim 1, wherein the at least one thermoplastic material is foamed during said extruding step.

9. The method of claim 1, wherein, after said extruding step, the thermoplastic material is pressed onto the first layer by a cooled roll.

10. The method of claim 1, wherein a thermoplastic polyurethane material is used as the thermoplastic material in step ii).

11. The method of claim 1, wherein the at least one thermoplastic material is foamed after said extruding step.

12. A substantially uninterrupted wound cover, said wound cover comprising
    a first layer of a foam material, having a first main area and a second main area; and
    a second layer of a thermoplastic film material as a germ barrier, which second layer is directly adjacent to the first main area of the first layer, and wherein the thermoplastic material of the second layer penetrates not more than 0.01 mm into the foam material of the first layer.

13. The wound cover of claim 12, obtained by steps of
    i) providing the foam material of the first layer; and
    ii) extruding the at least one thermoplastic material onto the foam material at a temperature above the softening temperature of the thermo-plastic material, and solidifying the material to form the second layer, while limiting penetration of the thermoplastic material of the second layer into the foam material of the first layer to not more than 0.01 mm.

* * * * *